(12) United States Patent
Dusch et al.

(10) Patent No.: US 11,468,990 B2
(45) Date of Patent: Oct. 11, 2022

(54) PREVENTION OF COMPUTER VISION SYNDROME USING EXPLAINABLE ARTIFICIAL INTELLIGENCE

(71) Applicant: KYNDRYL, INC., New York, NY (US)

(72) Inventors: William G. Dusch, Morrisville, NC (US); MacDonald Isere, Durham, NC (US); Nicholas L. Graham, Raleigh, NC (US); Scott Carrier, New Hill, NC (US)

(73) Assignee: KYNDRYL, INC., New York, NY (US)

( * ) Notice: Subject to any disclaimer, the term of this patent is extended or adjusted under 35 U.S.C. 154(b) by 107 days.

(21) Appl. No.: 17/067,878

(22) Filed: Oct. 12, 2020

(65) Prior Publication Data

US 2022/0115128 A1    Apr. 14, 2022

(51) Int. Cl.
*G16H 50/20* (2018.01)
*G16H 70/60* (2018.01)
*G16H 50/70* (2018.01)
*G16H 20/00* (2018.01)
*G16H 50/30* (2018.01)
(Continued)

(52) U.S. Cl.
CPC .............. *G16H 50/20* (2018.01); *A61B 5/486* (2013.01); *G09B 19/00* (2013.01); *G16H 20/00* (2018.01); *G16H 50/30* (2018.01); *G16H 50/50* (2018.01); *G16H 50/70* (2018.01); *G16H 70/60* (2018.01); *A61B 3/113* (2013.01)

(58) Field of Classification Search
USPC ........................................................ 705/2–3
See application file for complete search history.

(56) References Cited

U.S. PATENT DOCUMENTS 8,810,413 B2    8/2014  Wong
9,690,988 B2 *  6/2017  Mohanakrishnan ........................
                                                G06V 20/597
(Continued)

FOREIGN PATENT DOCUMENTS

AT       5066671 B1    10/2009
KR   101533853 B1     6/2015
(Continued)

OTHER PUBLICATIONS

Anshel, OD., Jeffrey R., et al., "Visual Ergonomics in the Workplace", AAOHN Journal 55.10: 414-420. Thorofare: Sage Publications, Inc. (Oct. 2007). (Year: 2007).*
(Continued)

*Primary Examiner* — Amber A Misiaszek
(74) *Attorney, Agent, or Firm* — Erik Swanson; Andrew M. Calderon; Calderon Safran & Cole P.C.

(57) ABSTRACT

Technology for applying explainable artificial training algorithms (XAI) to training machine learning algorithms for identifying potentially developing computer vision syndrome (CVS), CVS and/or recommended remedial action(s) that a user can perform to counter potentially developing CVS and/or existing CVS. In some embodiments, the XAI includes a Contrastive Explainability model. In some embodiments, the training performed by the XAI includes assigning weight factors respectively to CVS input parameters (for example, blink rate) based upon how strong the respective CVS input factor is correlated with development of CVS in the user.

20 Claims, 5 Drawing Sheets

(51) Int. Cl.
- *A61B 5/00* (2006.01)
- *G09B 19/00* (2006.01)
- *G16H 50/50* (2018.01)
- *A61B 3/113* (2006.01)

(56) References Cited

U.S. PATENT DOCUMENTS

| | | | |
|---|---|---|---|
| 10,281,980 | B2 | 5/2019 | Ayoub |
| 2007/0037664 | A1* | 2/2007 | Kaplan ............ A61H 5/00 482/1 |
| 2013/0012789 | A1 | 1/2013 | Horseman |
| 2017/0127055 | A1 | 5/2017 | Khabiri |
| 2017/0293356 | A1 | 10/2017 | Khaderi |
| 2019/0038129 | A1* | 2/2019 | Ong ............ A61B 3/10 |
| 2019/0290118 | A1 | 9/2019 | Jha |
| 2020/0314416 | A1* | 10/2020 | Sinha ............ G09G 3/2088 |
| 2021/0142765 | A1* | 5/2021 | Malhotra ............ G09G 5/10 |

FOREIGN PATENT DOCUMENTS

| | | |
|---|---|---|
| WO | 2007101712 A2 | 9/2007 |
| WO | 2009121088 A2 | 10/2009 |

OTHER PUBLICATIONS

"Using Light Sensors", Web API's, MDN web docs, downloaded from the internet on Apr. 20, 2020, 3 pages, <https://developer.mozilla.org/en-US/docs/Web/API/DeviceLightEvent/Using_light_sensors>.

"What Web Can Do Today: Ambient Light", downloaded from the internet on Apr. 20, 2020, 5 pages, <https://whatwebcando.today/ambient-light.html>.

"A Facial Recognition Based Feedback System for Managing Distance between Device and User." An IP.com Prior Art Database Technical Disclosure, Authors et. al.: Disclosed Anonymously, IP.com No. IPCOM000244810D, IP.com Electronic Publication Date: Jan. 18, 2016, 7 pages.

"Method for Changing Characteristics of Computer System Based upon User Fatigue Detection." An IP.com Prior Art Database Technical Disclosure, Authors et. al.: Disclosed Anonymously, IPCOM000241044D, IP.com No. IPCOM000241044D, IP.com Electronic Publication Date: Mar. 23, 2015, 5 pages.

Dhurandhar et al., "Explanations based on the Missing: Towards Contrastive Explanations with Pertinent Negatives", 32nd Conference on Neural Information Processing Systems (NIPS 2018), Montreal Canada, 12 pages.

Divjak et al., "Eye blink based fatigue detection for prevention of Computer Vision Syndrome", MVA2009 IAPR Conference on Machine Vision Applications, May 20-22, 2009, Yokohama, Japan, 4 pages.

Hossain, et al., "A Real-Time Face to Camera Distance Measurement Algorithm Using Object Classification", 1st International Conference on Computer & Information Engineering, Nov. 26-27, 2015, Organizer: Dept. of CSE, Rajshahi University of Engineering & Technology, Rajshahi, Bangladesh, 4 pages.

IBM, "Prevention of Computer Vision Syndrome." An IP.com Prior Art Database Technical Disclosure, Original Publication Date: Apr. 10, 2008, IP.com No. IPCOM000169193D, IP.com Electronic Publication Date: Apr. 10, 2008, 3 pages.

Kinlan, Paul, "Getting started with the Ambient Light Sensor", Jul. 13, 2018, 9 pages, <https://paul.kinlan.me/getting-started-with-the-ambient-light-sensor/>.

Li, et al., "Look into My Eyes: Fine-grained Detection of Face-screen Distance on Smartphones", arXiv:1612.04131v1 [cs.NI] Dec. 13, 2016, 8 pages.

Perez, Sarah, "Google Maps' "Night Mode" Feature Makes It Easier to Navigate in the Dark", Aug. 7, 2015, Tech Crunch, 2 pages, <https://techcrunch.com/2015/08/07/google-maps-new-night-mode-feature-makes-it-easier-to-navigate-in-the-dark/>.

Rios et al., "Prediction of Computer Vision Syndrome in Health Personnel by Means of Genetic Algorithms and Binary Regression Trees." Sensors 2019, 19, 2800; doi:10.3390/s19122800, Published: Jun. 22, 2019, 14 pages.

Zhang et al., "A New Real-Time Eye Tracking for Driver Fatigue Detection", 2006 6th International Conference on ITS Telecommunications Proceedings, 4 pages.

* cited by examiner

PREVENTION OF COMPUTER VISION SYNDROME USING EXPLAINABLE ARTIFICIAL INTELLIGENCE

BACKGROUND

The present invention relates generally to the field of computer vision syndrome, and also to the field of machine learning (ML).

The Wikipedia entry for "computer vision syndrome" (as of 18 Mar. 2020) states, in part, as follows: "Computer vision syndrome (CVS) is a condition resulting from focusing the eyes on a computer or other display device for protracted, uninterrupted periods of time and the eye muscles being unable to recover from the strain due to a lack of adequate sleep . . . . Some symptoms of CVS include headaches, blurred vision, neck pain, fatigue, eye strain, dry eyes, irritated eyes, double vision, vertigo/dizziness, polyopia, and difficulty refocusing the eyes. These symptoms can be further aggravated by improper lighting conditions (i.e. glare, strong blue-spectrum backlights, or bright overhead lighting) or air moving past the eyes (e.g. overhead vents, direct air from a fan) . . . . When working on computer screens people tend to blink less which leads to the eyes drying out faster. Reminding people to blink or do blinking exercises is achieved via static reminders (such as eyeleo). Real-time feedback based blink reminders (such as Vision-Protect) actively measure the blinking rate of the user and notify the user via visual/audial alert . . . . Americans spend an average of 8 hours a day in front of a screen, whether that be a television screen, phone/tablet, or a computer screen. This has increased the prevalence of individuals affected by computer vision syndrome." (footnotes omitted)

The Wikipedia entry for "explainable artificial intelligence" (as of 22 Mar. 2020) states, in part, as follows: "Explainable AI (XAI) refers to methods and techniques in the application of artificial intelligence technology (AI) such that the results of the solution can be understood by human experts. It contrasts with the concept of the 'black box' in machine learning where even their designers cannot explain why the AI arrived at a specific decision. XAI is an implementation of the social right to explanation . . . . AI systems optimize behavior to satisfy a mathematically-specified goal system chosen by the system designers, such as the command 'maximize accuracy of assessing how positive film reviews are in the test dataset'. The AI may learn useful general rules from the test-set, such as 'reviews containing the word 'horrible" are likely to be negative'. However, it may also learn inappropriate rules, such as 'reviews containing 'Daniel Day-Lewis' are usually positive'; such rules may be undesirable if they are deemed likely to fail to generalize outside the test set, or if people consider the rule to be 'cheating' or 'unfair'. A human can audit rules in an XAI to get an idea how likely the system is to generalize to future real-world data outside the test-set. Cooperation between agents, in this case algorithms and humans, depends on trust. If humans are to accept algorithmic prescriptions, they need to trust them. Incompleteness in formalization of trust criteria is a barrier to straightforward optimization approaches. For that reason, interpretability and explainability are posited as intermediate goals for checking other criteria. AI systems sometimes learn undesirable tricks that do an optimal job of satisfying explicit pre-programmed goals on the training data, but that do not reflect the complicated implicit desires of the human system designers." (footnotes omitted)

SUMMARY

According to an aspect of the present invention, there is a method, computer program product and/or system that performs the following operations (not necessarily in the following order): (i) receiving a potentially developing computer vision syndrome (PDCVS) input parameters data set indicating an identity of a plurality of input parameters that may be useful in determining whether computer vision syndrome (CVS) is potentially developing in users; (ii) receiving a plurality of PDCVS training data sets (PDCVS TDSs), with each given PDCVS TDS including information indicative of: (a) a plurality of PDCVS values corresponding to the plurality of input parameters, and (b) an indication of whether an individual subject of the given PDCVS TDS was experiencing potentially developing CVS; and (iii) training, by machine logic and based upon the plurality of PDCVS TDSs, a CVS determination machine learning algorithm that is structured and/or programmed to determine potentially developing CVS in users. The training includes assigning a respective weight factor to each PDCVS input parameter.

According to a further aspect of the present invention, there is a method, computer program product and/or system that performs the following operations (not necessarily in the following order): (i) receiving a plurality of computer vision syndrome input parameters data set indicating an identity of a plurality of input parameters that may be useful in determining a degree of computer vision syndrome (CVS) in users; (ii) receiving a plurality of CVS training data sets (CVS TDSs), with each given CVS TDS including information indicative of: (i) a plurality of CVS values corresponding to the plurality of input parameters, and (ii) an indication of a degree of CVS in an individual that is the subject of the given CVS TDS; and (iii) training, by machine logic of an explainable artificial intelligence algorithm (XAI), a CVS determination machine learning algorithm to obtain a trained CVS determination machine learning algorithm that is structured and/or programmed to determine a degree of CVS in users based upon the plurality of CVS TDSs. The training includes assigning a respective weight factor to each CVS input parameter.

According to a further aspect of the present invention, there is a method, computer program product and/or system that performs the following operations (not necessarily in the following order): (i) receiving a plurality of computer vision syndrome input parameters data set indicating an identity of a plurality of input parameters that may be useful in determining a degree of computer vision syndrome (CVS) in users; (ii) receiving a plurality of CVS training data sets (CVS TDSs), with each given CVS TDS including information indicative of: (i) a plurality of CVS values corresponding to the plurality of input parameters, and (ii) an indication of a degree of CVS in an individual that is the subject of the given CVS TDS; and (iii) training, by machine logic of an explainable artificial intelligence algorithm (XAI), a CVS determination machine learning algorithm to obtain a trained CVS determination machine learning algorithm that is structured and/or programmed to determine a degree of CVS in users based upon the plurality of CVS TDSs. The training includes mapping, in the trained CVS determination machine learning algorithm, various degrees of CVS respectively to sets remediative action(s), if any, to be recommended to users.

DETAILED DESCRIPTION

Figure 1:
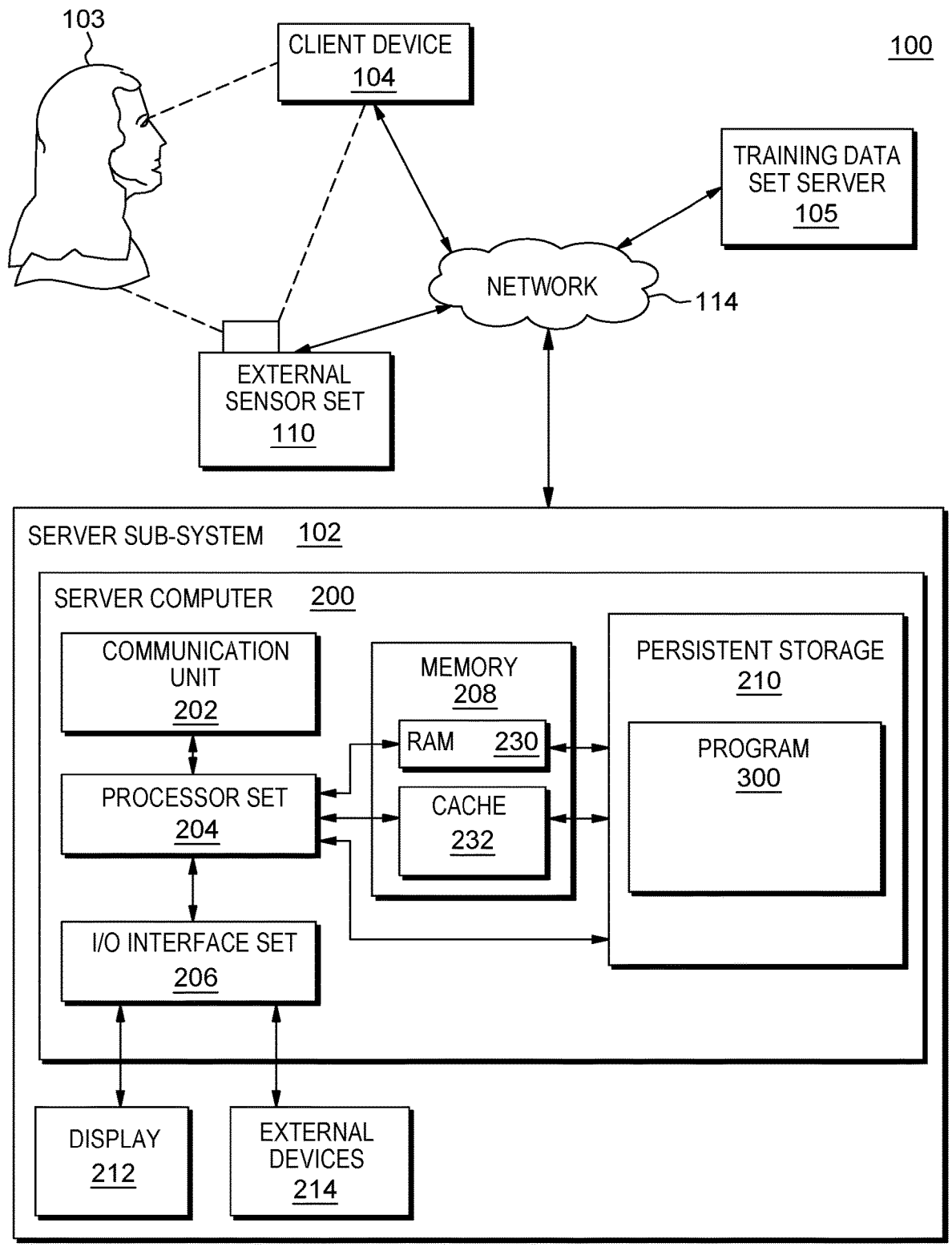
FIG. 1 is a block diagram of a first embodiment of a system according to the present invention.

This Detailed Description section is divided into the following subsections: (i) The Hardware and Software Environment; (ii) Example Embodiment; (iii) Further Comments and/or Embodiments; and (iv) Definitions.

I. The Hardware and Software Environment

The present invention may be a system, a method, and/or a computer program product at any possible technical detail level of integration. The computer program product may include a computer readable storage medium (or media) having computer readable program instructions thereon for causing a processor to carry out aspects of the present invention. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (for example, light pulses passing through a fiber-optic cable), or electrical signals transmitted through a wire.

A "storage device" is hereby defined to be anything made or adapted to store computer code in a manner so that the computer code can be accessed by a computer processor. A storage device typically includes a storage medium, which is the material in, or on, which the data of the computer code is stored. A single "storage device" may have: (i) multiple discrete portions that are spaced apart, or distributed (for example, a set of six solid state storage devices respectively located in six laptop computers that collectively store a single computer program); and/or (ii) may use multiple storage media (for example, a set of computer code that is partially stored in as magnetic domains in a computer's non-volatile storage and partially stored in a set of semiconductor switches in the computer's volatile memory). The term "storage medium" should be construed to cover situations where multiple different types of storage media are used.

Computer readable program instructions described herein can be downloaded to respective computing/processing devices from a computer readable storage medium or to an external computer or external storage device via a network, for example, the internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As shown in FIG. 1, networked computers system 100 is an embodiment of a hardware and software environment for use with various embodiments of the present invention. Networked computers system 100 includes: server subsystem 102 (sometimes herein referred to, more simply, as subsystem 102); user 103; client device 104; training data server 105; external sensor data set 110; and communication network 114. Server subsystem 102 includes: server computer 200; communication unit 202; processor set 204; input/output (I/O) interface set 206; memory 208; persistent storage 210; display 212; external device(s) 214; random access memory (RAM) 230; cache 232; and program 300. Client device 104 includes a display, which is the primary thing that user 103 is focusing her vision on over time. Both client device 104 and external sensor set 110 monitor the actions and contextual environment of user 103 and her gaze upon the display screen of client device 104.

Subsystem 102 may be a laptop computer, tablet computer, netbook computer, personal computer (PC), a desktop computer, a personal digital assistant (PDA), a smart phone, or any other type of computer (see definition of "computer" in Definitions section, below). Program 300 is a collection of machine readable instructions and/or data that is used to create, manage and control certain software functions that will be discussed in detail, below, in the Example Embodiment subsection of this Detailed Description section.

Subsystem 102 is capable of communicating with other computer subsystems via communication network 114. Network 114 can be, for example, a local area network (LAN), a wide area network (WAN) such as the internet, or a combination of the two, and can include wired, wireless, or fiber optic connections. In general, network 114 can be any combination of connections and protocols that will support communications between server and client subsystems.

Subsystem 102 is shown as a block diagram with many double arrows. These double arrows (no separate reference numerals) represent a communications fabric, which provides communications between various components of subsystem 102. This communications fabric can be implemented with any architecture designed for passing data and/or control information between processors (such as microprocessors, communications and network processors, etc.), system memory, peripheral devices, and any other hardware components within a computer system. For example, the communications fabric can be implemented, at least in part, with one or more buses.

Memory 208 and persistent storage 210 are computer-readable storage media. In general, memory 208 can include any suitable volatile or non-volatile computer-readable storage media. It is further noted that, now and/or in the near future: (i) external device(s) 214 may be able to supply, some or all, memory for subsystem 102; and/or (ii) devices external to subsystem 102 may be able to provide memory for subsystem 102. Both memory 208 and persistent storage 210: (i) store data in a manner that is less transient than a signal in transit; and (ii) store data on a tangible medium (such as magnetic or optical domains). In this embodiment, memory 208 is volatile storage, while persistent storage 210 provides nonvolatile storage. The media used by persistent storage 210 may also be removable. For example, a removable hard drive may be used for persistent storage 210. Other examples include optical and magnetic disks, thumb drives, and smart cards that are inserted into a drive for transfer onto another computer-readable storage medium that is also part of persistent storage 210.

Communications unit 202 provides for communications with other data processing systems or devices external to subsystem 102. In these examples, communications unit 202 includes one or more network interface cards. Communications unit 202 may provide communications through the use of either or both physical and wireless communications links. Any software modules discussed herein may be downloaded to a persistent storage device (such as persistent storage 210) through a communications unit (such as communications unit 202).

I/O interface set 206 allows for input and output of data with other devices that may be connected locally in data communication with server computer 200. For example, I/O interface set 206 provides a connection to external device set 214. External device set 214 will typically include devices such as a keyboard, keypad, a touch screen, and/or some other suitable input device. External device set 214 can also include portable computer-readable storage media such as, for example, thumb drives, portable optical or magnetic disks, and memory cards. Software and data used to practice embodiments of the present invention, for example, program 300, can be stored on such portable computer-readable storage media. I/O interface set 206 also connects in data communication with display 212. Display 212 is a display device that provides a mechanism to display data to a user and may be, for example, a computer monitor or a smart phone display screen.

In this embodiment, program 300 is stored in persistent storage 210 for access and/or execution by one or more computer processors of processor set 204, usually through one or more memories of memory 208. It will be understood by those of skill in the art that program 300 may be stored in a more highly distributed manner during its run time and/or when it is not running. Program 300 may include both machine readable and performable instructions and/or substantive data (that is, the type of data stored in a database). In this particular embodiment, persistent storage 210 includes a magnetic hard disk drive. To name some possible variations, persistent storage 210 may include a solid state hard drive, a semiconductor storage device, read-only memory (ROM), erasable programmable read-only memory (EPROM), flash memory, or any other computer-readable storage media that is capable of storing program instructions or digital information.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

II. Example Embodiment

Figure 2:
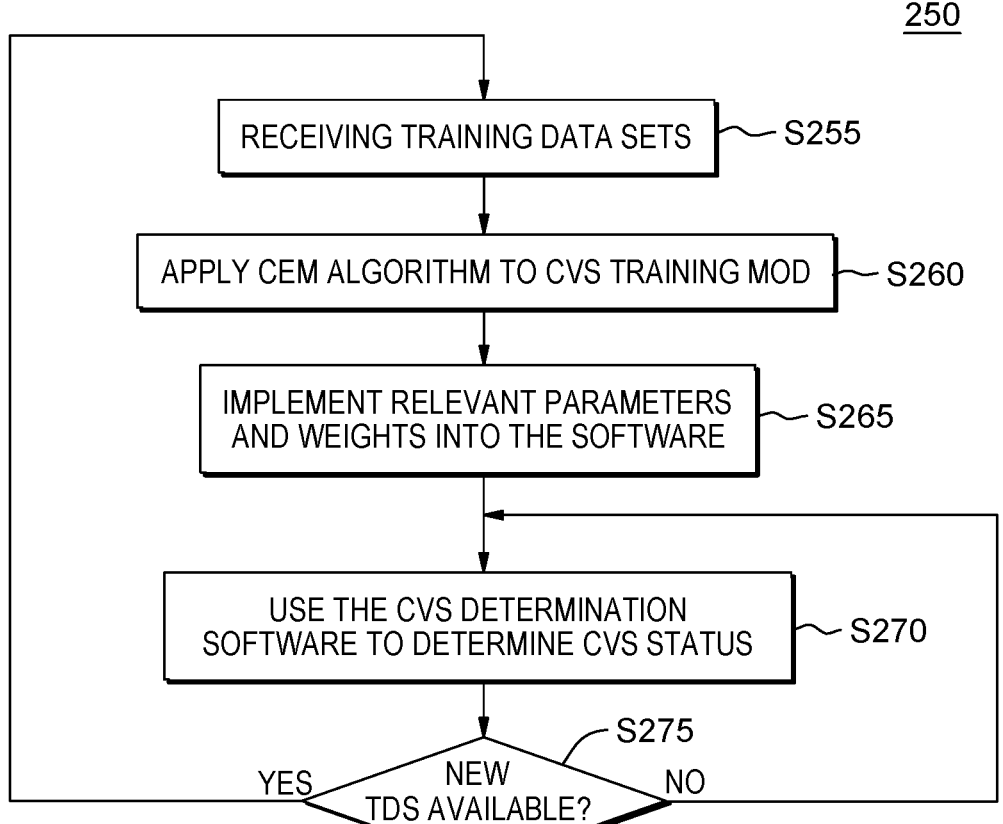
FIG. 2 is a flowchart showing a first embodiment method performed, at least in part, by the first embodiment system.
Figure 3:
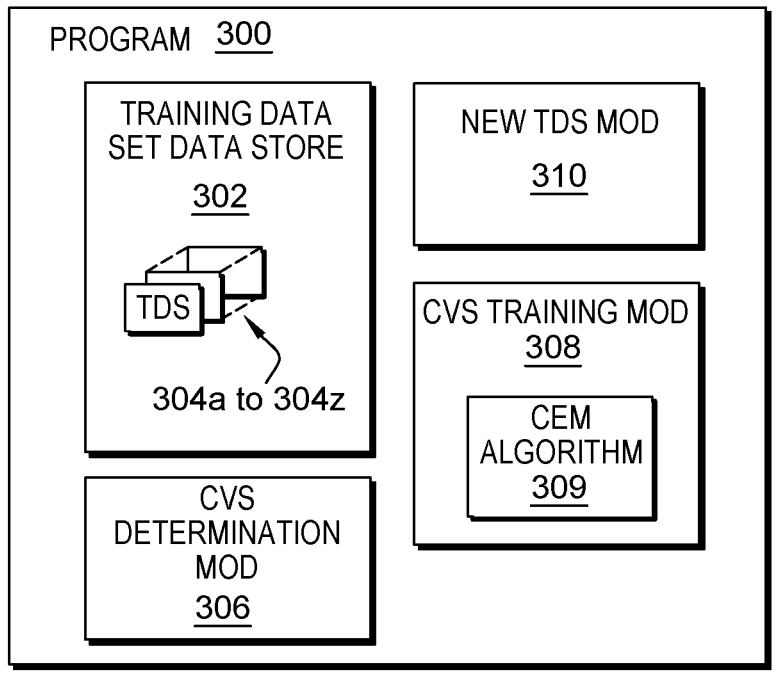
FIG. 3 is a block diagram showing a machine logic (for example, software) portion of the first embodiment system.

As shown in FIG. 1, networked computers system 100 is an environment in which an example method according to the present invention can be performed. As shown in FIG. 2, flowchart 250 shows an example method according to the present invention. As shown in FIG. 3, program 300 performs or controls performance of at least some of the method operations of flowchart 250. This method and associated software will now be discussed, over the course of the following paragraphs, with extensive reference to the blocks of FIGS. 1, 2 and 3.

Processing begins at operation S255, where training data set (TDS) data store 302 receives training data sets 304a to 304z, through communication network 114 and from training data set server 105. These training data sets are historical data. Roughly speaking, this historical data includes input values and output data.

In this example, for this method of identifying potential developing CVS (PDCVS), the input values in each TDS (sometimes herein referred to as "PDCVS related input parameters") are: blink rate value, ambient light level, ambient temperature, ambient barometric pressure, eye color, average distance between users eyes and screen, average viewing angle of the screen, proportion of time user is looking at screen, user mood, ambient pollen count, type of corrective lenses worn by user, user heart rate, average font size of text, font of text and amount of variation in user's depth of focus. Of course, not all of these input data dimensions in the TDSs will turn out to be relevant to PDCVS, but the machine learning is more robust if more dimensions in the training data are at least considered when developing and or refining the machine logic of CVS determination module ("mod") 306. Also, some input dimensions (or parameters) may have conditional importance. For example, in this hypothetical example, it is determined that pollen count is generally not relevant, unless the user is wearing contact lens type corrective lenses, in which case pollen count becomes the most important parameter to be considered when CVS determination mod determines whether a PDCVS condition is incipient or developing.

In this example, for this method of identifying potential developing CVS (PDCVS), the output values in each TDS (sometimes herein referred to as PDCVS historical determination values) are: whether user reported a current CVS condition, whether user reported a CVS condition 15 minutes earlier, and whether user reported a CVS condition 15 minutes later.

Processing proceeds to operation S260, where CVS training mod 308 trains CVS determination mod 306 using TDSs 304a to 304z. CVS determination mod 306 is a piece of machine logic used to determine incipient CVS and/or actual CVS. Mod 308 makes improvements to mod 306 under the process known as machine learning (ML). In this example, this training uses Contrastive Explainability Model (CEM) algorithm 309, which is a type of a category of algorithms herein referred to as "artificial intelligence explainability algorithms" (or "XAI algorithms," or, more simply, "XAI"). As the term is used herein, an XAI algorithm is any algorithm for execution by a set of computer processor(s) that includes the feature of "explainable AI" (as that term is defined, above, in the Background section). As the term is used herein, a Contrastive Explainability Model algorithm is any XAI algorithm that uses a Contrastive Explainability Model. The application of CEM algorithms, in the context of PDCVS, will now be explained in detail in the following paragraphs.

For each predetermined time interval (for example, each month), CEM algorithm 309 outputs: (i) a set of Pertinent Positives (PP), and (ii) a set of Pertinent Negatives (PN). The PP and PN are used for the purposes of ranking CVS related input parameters (for example, blink rate) with respect to the relative amount of influence a given CVS related input parameter has upon degradation in state towards eye fatigue (or CVS). These relative amounts of influence of various CVS related input parameters can then be used to recommend remediating actions for the user.

This paragraph will provide a summary of PP/PN features. Each CVS related input is classified by a neural network (not separately shown in FIGS. 1 and 3). Given the identity of the CVS related input and its classification value, CEM algorithm 309 creates explanations as follows: (i) algorithm 309 finds a minimal set of CVS related input parameters that are sufficient in themselves to yield the same classification (that is, PPs); (ii) algorithm 309 also finds a minimal amount of CVS related input parameters that should not be considered by the machine logic in rendering determinations of incipient CVS to prevent the classification result from changing (that is, PNs); and (iii) algorithm 309 performs the two foregoing operations "close" to the data manifold using a state-of-the-art convolutional autoencoder (CAE) (not separately shown in FIGS. 1 and 3) to get more "realistic" explanations from the XAI algorithm that is CEM algorithm 309.

The previous paragraph explains how PPs and PNs are used in ranking or weighting various CVS related input parameters. Alternatively or additionally, PPs and PNs can also be used to help CVS determination mod 306 to better recommend the most effective remediating actions the user can take to counter potentially developing eyestrain. Pertinent Positives (PP) and Pertinent Negatives (PN) can be used for recommending remediating actions to a user as follows: (i) evaluate PP/PN features across prediction intervals, identifying feature deviations between the intervals, which provides clues as to the voltage deviations in features from one state transition prediction interval to the next and so on; (ii) receive a set of remediating actions, including polarity actions (for example, "turn on a light in your environment" OR "dim your screen", but don't do both); (iii) the features themselves, as a feature moves between PP and PN sets within our state prediction model as well as the degree of value changes are used to determine the voltage (impact) of a feature with respect to predicted state transitions over time; and (iv) analyze the predefined remediating actions corresponding to the high voltage features/values and rank them according to the impact of a feature or features over the time intervals, across the different state transitions as the designated threshold of generally low or no eye fatigue is crossed towards a degrading state of eye fatigue. Further with respect to item (ii) in the foregoing list, remediating actions are mapped to an individual feature or a set of features and/or value-thresholds. These actions are predefined per embodiment and associated with one or more features/values with which the voltage of said features can be identified across prediction time intervals.

Figure 4A:
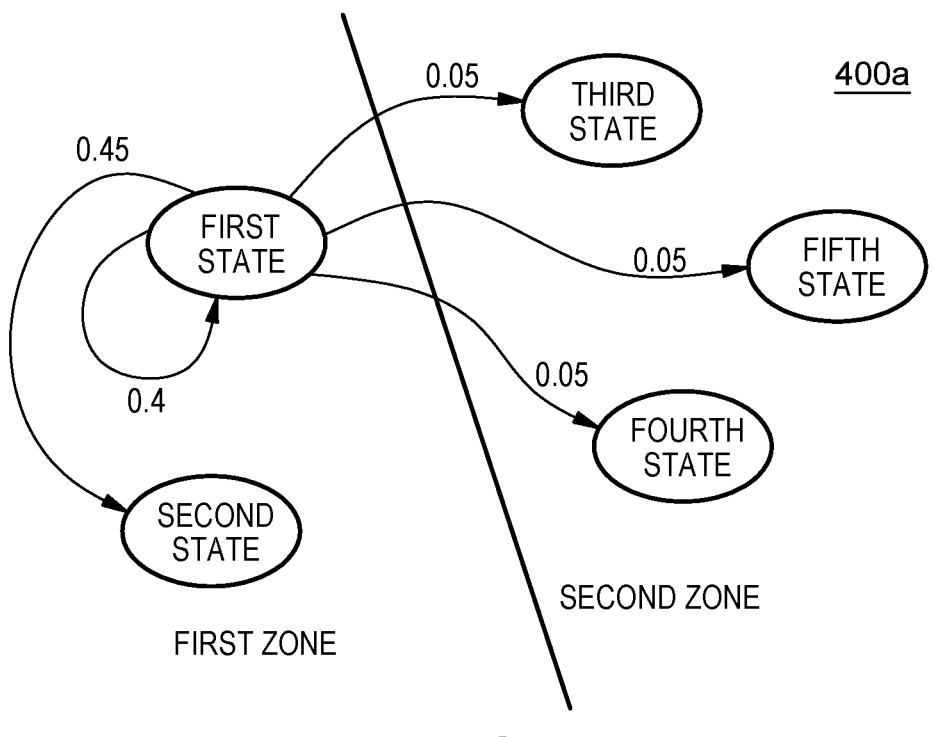
FIG. 4A is a state diagram illustrating an example according to the present invention.

A simplified illustration of a transition from a non-CVS state into a CVS state will now be discussed, with reference to diagram 400a of FIG. 4A. Diagram 400a includes a first state node, a second state node, a third state node, a fourth state node, a fifth state node and weighted paths (weighting factors shown in FIG. 4a) from the first state node to the various other nodes. In the example of diagram 400a, there are eye fatigue progression state transitions potentially among and between the first to fifth states (Markov chain). The first and second nodes are considered as being non-CVS. The third state is a transitional state between non-CVS and degrading to mild CVS (in the fourth state) and ultimately to full-blown CVS (in the fifth state). It is not a Boolean classification. Rather, the first to fifth states represent a fatigue progression scale with which the system designer can define a threshold of when to assert remediating actions. This threshold is shown as the dividing line between the first zone and the second zone in diagram 400a. In diagram 400a, a user is classified as first CVS related state (that is, no CVS) with predicted progression to the second state (still no CVS, so no remediating actions suggested at this time, but CVS determination mod 306 will, when it becomes operative after training, monitor at least some of the PDCVS input parameter values over time to determine whether these values indicate a potential transition across the alerting threshold.

Figure 4B:
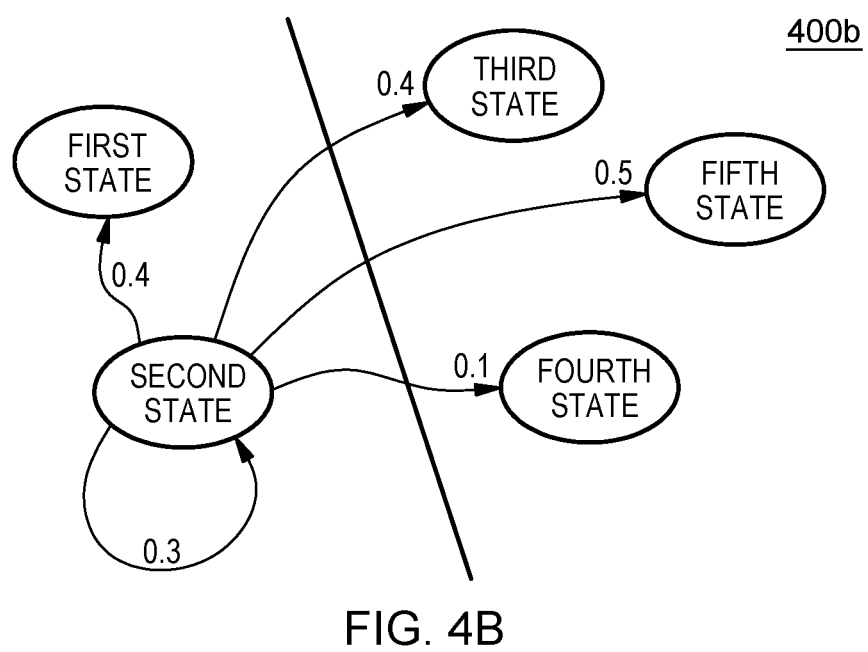
FIG. 4B is a is another state diagram illustrating an example according to the present invention.

As shown in diagram 400b of FIG. 4B, a user is classified as second state, which is non-CVS, but the machine logic of mod 306 predicts transition the third state 3, which is above the alerting threshold (that is, located in the second zone). In this simple example, there are two (2) time intervals with: (i) a state transition from first state to second state, as predicted in the first interval (see diagram 400a and the relative large 0.45 path weighting for the path from the first state node to the second state node); and (ii) a predicted transition of a state above the alert threshold (see diagram 400b and the relative large 0.4 path weighting for the path from the second state node to the third state node)). In many real-world embodiments, prediction intervals would be shorter, resulting in a multiplicity of data sets—this simple example is just for illustration.

From the PP/PN values, we can see that x2 came into play (PP), as did x5 (FN) with the predicted transition to state 3 in (see diagram 400b) from the PP/PN features identified in the predicted transition to state 2 in the prior time interval (see diagram 400a). These are features that mod 306 (after training by mod 308) determines as having some degree of voltage, with the PP features in this case being given more voltage (higher rank), since these features are contributory to the predicated state transition—this constitutes a ranked feature set. With the features now ranked, remediating actions associated with feature x2 are retrieved, as are remediating actions associated with x5. The resulting set of ranked remediating action are then suggested to the user, since we crossed the predicted state threshold for alerting the user. The prediction intervals continue on. Depending on the embodiment, an additional alerting threshold may come into play after the first alert, such that mod 306 does not communicate to the user remediating actions at each frequent prediction interval, but rather mod 306 allows for a window of time for the user to act upon the remediating actions and the outcomes of said actions to be borne out in subsequent prediction intervals.

This concludes the discussion of CEM style XAI algorithm 309, and its application to train CVS determination mod 306 with respect to: (i) determining, or refining, weight values for the various PDCVS input parameters when determining or predicting a CVS related state (in this example, first state, second state, third state, fourth state or fifth state); and/or (ii) determining, or refining, machine logic for determining whether, and which, counter-CVS measure recommendations should be given to user 103 at any given time.

Processing proceeds to operation S265 where CVS training mod 308 revises, adds to and/or subtracts from the various data (for example, threshold values), instructions and machine logic based rules of CVS determination mod 306 based on the training that was performed on mod 308 to obtain a new version of the machine logic of CVS training mod 306 (sometimes herein referred to as a post-training version of mod 306).

In this example, one of the parts of mod 306 that is revised, by newly trained mod 308) is the weight values respectively associated with various PDCVS input parameters. More specifically, after training by the CEM algorithm, the weights for the various PDCVS input parameters are revised in mod 306 to be as follows (weight values given in parentheses and are for users that do not wear corrective lenses): blink rate value (0.25), ambient light level (0.2), ambient temperature (0.05), ambient barometric pressure (0.0), eye color (0.0), average distance between users eyes and screen (0.25), average viewing angle of the screen (0.125), proportion of time user is looking at screen (0.0), user mood (0.0), ambient pollen count (0.0), type of corrective lenses worn by user (0.0), user heart rate (0.0), average font size of text (0.0), font of text (0.0) and amount of variation in user's depth of focus (0.125). Prior to the revisions to the machine logic of mod 306, made by newly-trained mod 308, the weight values for each of the foregoing parameters was equal. It is expected that mod 306 will better predict potential development of CVS in user 103 now that these weight values have been adjusted.

Processing proceeds to operation S270, where CVS determination mod 306: (i) receives CVS related input parameter values, for user 103 using the display screen of client device 104, from client device 104 and external sensor set 110; (ii)

determines when user 103 is not currently in a CVS state, but is likely to enter a CVS state in the next 15 minutes (that is, in a PDCVS state); and (iii) sends a communication to client device 104 with recommended remediating actions when user 103 enters a PDCVS state.

During the previous operation S270, processing intermittently proceeds to operation S275, where new TDS mod 310 determines whether there is new training data sets available from training data set server 105. If there are new TDS, then processing proceeds back to operation S255. If there are not new TDS, then processing proceeds back to the normal CVS detection operation of operation S270.

III. Further Comments and/or Embodiments

Some embodiments of the present invention recognize one, or more, of the following facts, potential problems and/or potential areas for improvement with respect to the current state of the art: (i) Computer Vision Syndrome (CVS) is a condition that affects 90% of people who work on computers for three hours a day or more; (ii) this affects a lot of employees' wellness and productivity; (iii) the causes of CVS are well known, and actions which prevent it are typically ignored by people; (iv) there is a need for a cognitive solution to predict an increased transition in CVS; and/or (v) there is a need for a cognitive solution to feed this to provide recommended actions a user can take based on the most important factors predicting the increase in CVS taken from an explanation of the AI algorithm (that is, an "XAI algorithm").

Some embodiments of the present invention may include one, or more, of the following operations, features, characteristics and/or advantages: (i) adjusts display settings only after predicting a transition of eye fatigue; (ii) providing actions which can include display adjustment after finding the most important factors responsible for the user's increase in eye fatigue; (iii) uses light conditions as an environmental factor; (iv) takes into account the user's eye condition and other environmental sources and feeds them into an algorithm which predicts a change in the state of eye fatigue of the user; (v) actions can include adjusting the display, but those are predicted by the most important factors responsible for the user's increase in eye fatigue; (vi) accounts for facial features; (vii) includes environmental factors and takes feedback from the algorithm to take proposed actions; (viii) uses deep learning for feature extraction and generalization; (ix) involves prediction of a transition between fatigue states; (x) includes a predictive element—detecting eye fatigue and offering instructions for relaxations; and/or (xi) predicts transitions of fatigue, not just detection of existing fatigue, and offers prescriptive actions based off of possible causes, some of which can be automated.

Some embodiments of the present invention may include one, or more, of the following operations, features, characteristics and/or advantages: (i) given a computing device with a camera, identifying progressing eye fatigue over a period of time; (ii) determining a ranked list of sub-optimal device configurations and user posture in relation to the device; (iii) suggesting and/or previewing changes that could alleviate fatigue; and/or (iv) if user accepts the eye fatigue preventative suggestions, the system monitors for digression or slowing of fatigue (that is, did the suggested preventative measures help stave off eye fatigue).

Some embodiments of the present invention may include one, or more, of the following operations, features, characteristics and/or advantages: (i) method to predict in advance increasing symptoms of Computer Vision Syndrome (CVS) and make recommendations on remediating actions based on factors found to be most contributive to the condition; (ii) identifying sub-optimal conditions of device viewing configurations (brightness, font size) in relation to the surrounding environment (user too close to screen, bright or dim lighting), identifying and suggesting remediating actions, and monitoring the results; (iii) optimizing device settings for the environment in which it is being used, as well as other actions a user can take; (iv) using an AI explainability algorithm to prioritize actions taken after a prediction has been made; (v) ranked list of causal factors, including both device settings as well as environmental conditions; (vi) prescriptive list of remediating actions based on the causal factors; and/or (vii) can help employees work longer, improve the wellness of employees, and make them be more productive.

Figure 5:
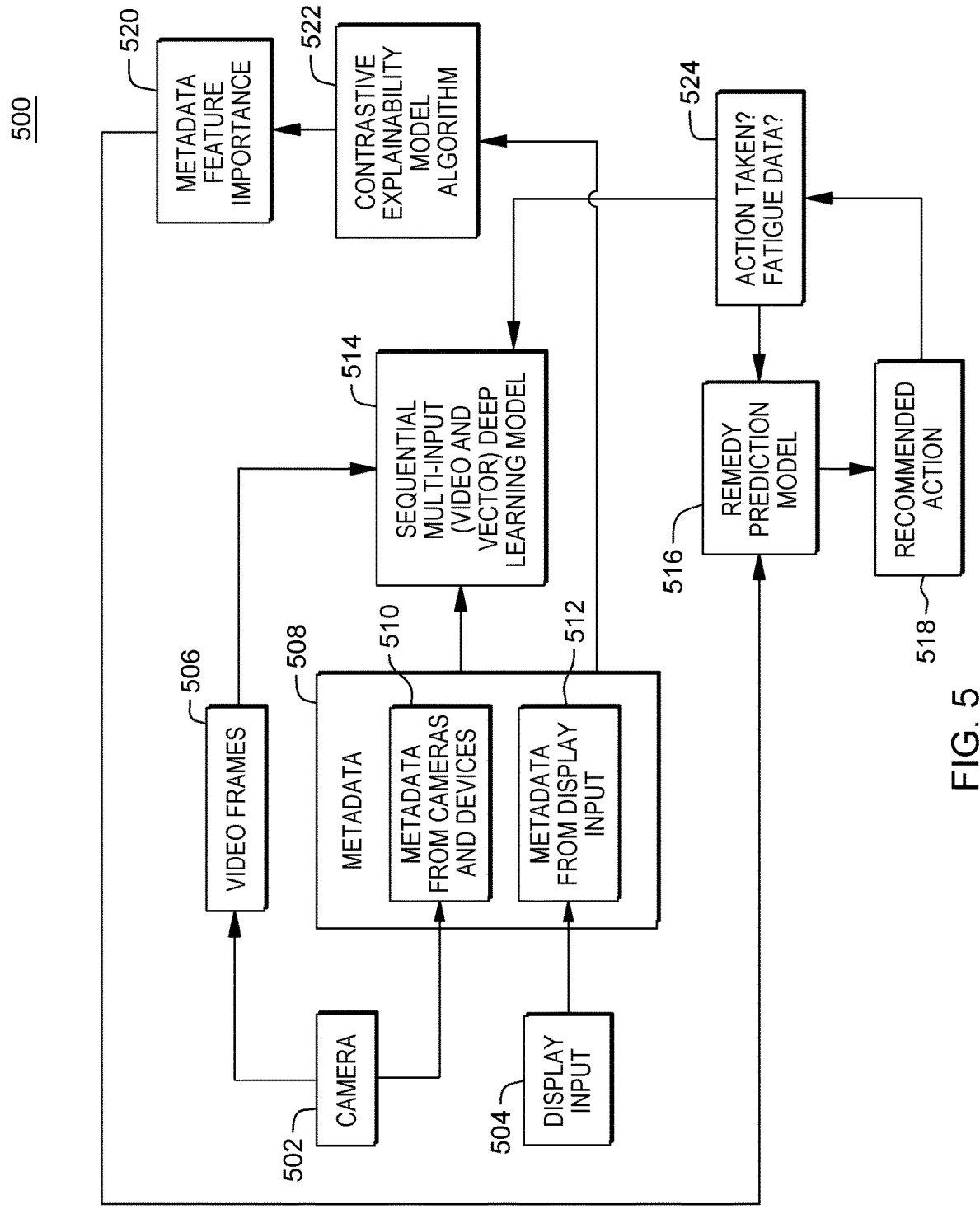
FIG. 5 is a block diagram of a second embodiment of a system according to the present invention.

As shown in FIG. 5, overview diagram 500 includes: camera block 502; display input block 504; video frames block 506; metadata block 508 (including metadata from camera and devices block 510 and metadata from display input block 512); sequential multi-input (video and vector) deep learning model block 514; remedy prediction model block 516; recommend action block 518; metadata feature importance block 520; contrastive explainability model algorithm block 522; and action and fatigue queries block 524.

A method according to an embodiment of the present invention includes the following operations (not necessarily in the following order): (i) photo/video snapshots of a user are periodically taken via a camera-enabled device (e.g. laptop, tablet, phone, etc.) with consent of the user to do so for the purpose of ameliorating eye fatigue; (ii) at each snapshot interval, device setting data as well as environmental conditions such as the ambient lighting, proximity of the user-to-device distance, etc. is gathered—this will be metadata fed into the machine learning model; (iii) classify whether there will an increase in the level of eye fatigue within the next timeframe (for example, 15 minutes, see block 514 in FIG. 1); (iv) use an AI (artificial intelligence) explainability algorithm on the classification prediction to get the most contributing factors for the prediction for the specific user (see diagram 500 at block 522) by performing the following sub-operations: (a) use a local, post-hoc, sample-based AI explanation algorithm (for example, Contrastive Explanation Method) to extract feature importance of the different features based on the algorithm for the given input into the model so that feature importance is calculated for the metadata fed into the model, and (b) using these calculated feature importance to prioritize which actions would be taken (see diagram 500 at block 520); (v) classify the remedies taken from the metadata feature importance (see diagram 500 at block 516) by performing the following sub-operations: (a) use a tabular machine learning algorithm, for example, gradient boosting, or a more explainable ML algorithm, and (b) feed in the metadata and outputs from contrastive explanations (for example, feature importance) of the metadata and feedback features to classify which remedy should be taken (note: there can be more than one remedy for the causes); (vi) recommend or automatically take actions based on most contributing factors and level of severity predicted (see diagram 500 at block 518) by using the output from the remedy classification algorithm to get a ranked list of remedies per cause; and (vii) acquire feedback information regarding whether the recommended action been has been taken by the user and whether the user's degree of fatigue has decreased after the action has been taken. Further with regard to step (vii), these features are fed back into the eye fatigue transition prediction model and the remedy prediction model.

Further with regard to step (ii) set forth in the previous paragraph: (a) this operation may be performed, at least in part, by publically available ambient light art; and (b) this operation may be performed, at least in part by publicly available face proximity art. Further with regard to operation (iii) set forth in the previous paragraph: (a) some embodiments may use a visual recognition deep learning algorithm to classify this (for example, a CNN (convolutional neural network) fed in a larger sequential RNN (recurrent neural network) or other sequential deep learning network—by taking the video, instead of trying to predict from a single video frame alone, this method takes a window of frames to feed into the algorithm, (b) some embodiments feed into the extracted factors as metadata to feed into the algorithm, such as distance, environmental conditions, and feedback features, calculated in a temporal sequence of the same window as the video, (c) another approach could be to take the current video frame and metadata, which may be a less accurate method for prediction than the sequence of frames plus metadata, (d) the algorithm would predict a Markov chain to predict the probability of transitioning to a different state of fatigue or staying the same state of fatigue within the 15 minute time window, and (e) next operation (iv) occurs if the transition probability to the next level of fatigue is high enough. Further with respect to operation (vi) in the previous paragraph: (a) an example output is as follows: "It is recognized that there are two important causes—either turn on a light, or get under better lighting, or adjust your screen size," and (b) some changes, such as, for example, automatically adjusting brightness could also be automated.

Figure 6:
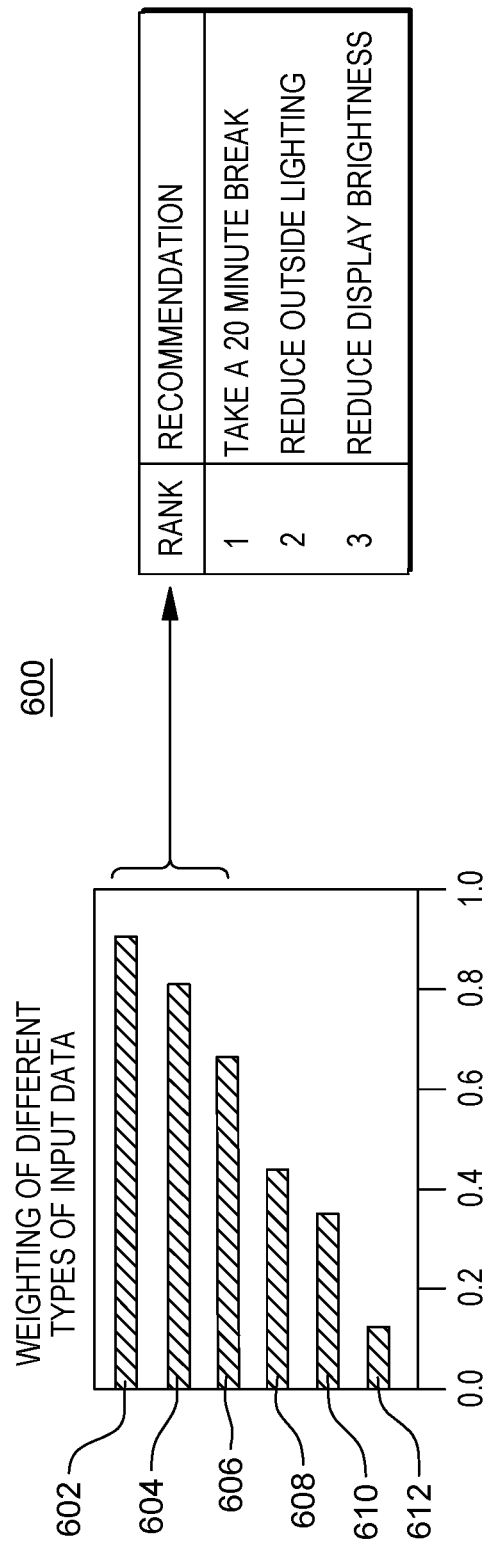
FIG. 6 is a diagram helpful in understanding various embodiments.

As shown in FIG. 6, diagram 600 shows an example output of the method set forth two paragraphs previous. It is noted that FIG. 6 weighs different inputs with different weighting factors. In some embodiments, the values for these weighting factors may be determined and/or refined by machine learning. In diagram 600: bar 602 represents the weighting factor for the PDCVS input parameter of time spent looking at a display screen; bar 604 represents the weighting factor of the PDCVS input parameter of ambient light; bar 606 represents the weighting factor of the PDCVS input parameter of display brightness; bar 608 represents the weighting factor of the PDCVS input parameter of proximity; bar 610 represents the weighting factor of the PDCVS input parameter of time of day; and bar 612 represents the weighting factor of the PDCVS input parameter of font size.

A method according to an embodiment of the present invention includes the following operations (not necessarily in the following order): (i) photo/video snapshots of a user are periodically taken via a camera-enabled device; (ii) at each snapshot interval, device setting data as well as environmental conditions such as the ambient lighting, proximity of the user-to-device distance, etc. is gathered; (iii) determine whether there will be an increase in the level of eye fatigue within the next timeframe (for example, 15 minutes); (iv) use an AI algorithm on the classification prediction to determine factors which contribute most to the increase in eye fatigue for the specific user; (v) classify potential remedies based on the factors determined to contribute most; and (vi) recommend or automatically take actions based on most contributing factors and level of severity predicted.

Some embodiments of the present invention are directed to a method for predicting a progression toward the onset of eye fatigue (or CVS) rather than detecting that a user already has eye fatigue (or CVS). In these embodiments: (i) users are alerted to remediating actions before they have already entered a fatigue state; (ii) users are alerted to a predicted progression towards an eye fatigue (or CVS) state; and (iii) this allows them to take remediating actions before they actually cross the threshold that is considered to divide eye fatigue from non-fatigued states (or dividing CVS from non-CVS states).

Some embodiments of the present invention may include one, or more, of the following operations, features, characteristics and/or advantages: (i) does not merely predict that generally the user might in the future experience eye fatigue or merely estimate that the user is currently experiencing eye fatigue; (ii) rather, the prediction is that between the current snapshot and a specific next time frame (for example, 15 minutes, next snapshot, etc.); (iii) it is predicted, based on the factors discussed herein, that the user will likely experience eye fatigue and which factors are the most relevant to that prediction; (iv) uses a feedback loop where the system can track whether a suggested remedial action was undertaken and whether it helped this specific user; and/or (v) the feedback loop of the previous item on this list can be used to provide data for additional training sets so that machine learning can occur with respect to computerized determinations of CVS or trending toward CVS.

Some embodiments of the present invention may include one, or more, of the following operations, features, characteristics and/or advantages: (i) a method of providing meaningful instruction to the user in regards to the remediating steps; (ii) provides specific remediating actions to the user; (iii) the actions presented to the user are specific to that particular user and the specific environment and time in which they are working; (iv) the ranked set of actions may span both changes in their environment and/or the device they are operating; and/or (v) the actions are derived from the most contributory features extracted from the prediction models, that are then fed through an explainability algorithm, and converted to actions conveyed in natural language that a user can understand and act upon to prevent entering a fatigue state.

Some embodiments of the present invention may include one, or more, of the following operations, features, characteristics and/or advantages: (i) use of ML to predict a progression towards eye fatigue state rather than classifying that the user is currently in a fatigue state; (ii) includes a prediction model which acts as the source from which the most contributory factors to the progression towards eye fatigue state for that user and his/her environment at that specific moment in time; and/or (iii) ultimately generates a recommendation for meaningful, ranked actions a user can perform to stave off entering a fatigue state.

Some embodiments of the present invention may include one, or more, of the following operations, features, characteristics and/or advantages: (i) takes periodic snapshots of the conditions surrounding the user and then predicting that there will be a state change by the next snapshot (for example, eye fatigue will occur between those snapshots); (ii) ranking the factors that are most important or contribute most to that prediction; (iii) determining a ranking for the influence each factor has and then making a recommendation based on the ranking; (iv) determining a ranking of influence for different factors and making recommendations based on the determined rankings; (v) determines which factors, relevant to eyestrain, are more relevant to a given prediction of eye fatigue (for example, which factors contributed most to the prediction of eye fatigue); (vi) ranks multiple conditions on their relative contribution to a prediction of eye fatigue; (vii) includes a feedback loop directed to improving the calculated relevance/contribution of different factors to adjust rankings and, hence, the suggestions provided; (viii) determines the relative importance levels for of the different factors to a prediction and providing suggestions based on which factors are most important rather than just providing suggestions on all contributing factors; and/or (ix) a feedback loop that adjusts the ranking based on the feedback through the machine learning and observation to ultimately improve not just the prediction of eye fatigue, but also to alter which suggestions are provided.

IV. Definitions

Present invention: should not be taken as an absolute indication that the subject matter described by the term "present invention" is covered by either the claims as they are filed, or by the claims that may eventually issue after patent prosecution; while the term "present invention" is used to help the reader to get a general feel for which disclosures herein are believed to potentially be new, this understanding, as indicated by use of the term "present invention," is tentative and provisional and subject to change over the course of patent prosecution as relevant information is developed and as the claims are potentially amended.

Embodiment: see definition of "present invention" above—similar cautions apply to the term "embodiment."

and/or: inclusive or; for example, A, B "and/or" C means that at least one of A or B or C is true and applicable.

Including/include/includes: unless otherwise explicitly noted, means "including but not necessarily limited to."

Module/Sub-Module: any set of hardware, firmware and/or software that operatively works to do some kind of function, without regard to whether the module is: (i) in a single local proximity; (ii) distributed over a wide area; (iii) in a single proximity within a larger piece of software code; (iv) located within a single piece of software code; (v) located in a single storage device, memory or medium; (vi) mechanically connected; (vii) electrically connected; and/or (viii) connected in data communication.

Computer: any device with significant data processing and/or machine readable instruction reading capabilities including, but not limited to: desktop computers, mainframe computers, laptop computers, field-programmable gate array (FPGA) based devices, smart phones, personal digital assistants (PDAs), body-mounted or inserted computers, embedded device style computers, application-specific integrated circuit (ASIC) based devices.

What is claimed is:

1. A computer-implemented method comprising:
receiving a potentially developing computer vision syndrome (PDCVS) input parameters data set indicating an identity of a plurality of input parameters that may be useful in determining whether computer vision syndrome (CVS) is potentially developing in users, the PDCVS input parameters data set received from a plurality of external sensors monitoring actions of a user and contextual environment of the user;
receiving a plurality of PDCVS training data sets (TDSs), with each given PDCVS TDS including information indicative of: (i) a plurality of PDCVS values corresponding to the plurality of input parameters, and (ii) an indication of whether an individual subject of the given PDCVS TDS was experiencing potentially developing CVS, wherein the PDCVS TDSs comprise historical PDCVS input parameters data sets based on historical external sensor data;
training, by machine logic and based upon the plurality of PDCVS TDSs, a CVS determination machine learning algorithm that is structured and/or programmed to determine potentially developing CVS in users, the training resulting in a trained CVS determination machine learning algorithm, wherein the training includes assigning a respective weight factor to each PDCVS input parameter;
identifying, by the trained CVS determination machine learning algorithm, factors that contribute more, relative to other factors, to PDCVS of the user based on the respective weight factors of the PDCVS input parameters; and
performing an action selected based on the identified factors of the trained CVS determination machine learning algorithm,
wherein the computer implemented method is configured to select the action comprising at least one of recommending actions to the user to prevent CVS and automatically making environmental changes to protect the user from CVS.

2. The computer-implemented method of claim 1 wherein the plurality of PDCVS input parameters include at least one of the following: time spent looking at a display screen, ambient light, display brightness, proximity, time of day and font size.

3. The computer-implemented method of claim 1 wherein the plurality of PDCVS input parameters include all of the following: time spent looking at a display screen, ambient light, display brightness, proximity, time of day and font size.

4. The computer-implemented method of claim 1 further comprising:
defining, in machine logic of the CVS determination machine learning algorithm, a plurality of nodes respectively corresponding to a plurality of CVS related states including: (i) a first set of CVS related state(s) indicating no current CVS and no PDCVS, (ii) a second set of CVS related state(s) indicating PDCVS, and (iii) a third set of CVS related state(s) indicating current CVS.

5. The computer-implemented method of claim 4 further comprising:
receiving a plurality of PDCVS input parameter values, corresponding to the plurality of PDCVS input parameters, that have been determined for a first user at a first time;
assigning, to the first user and by the CVS determination machine learning algorithm, a first CVS related state, from the plurality of CVS related states, based on the plurality of PDCVS input parameter values as weighted by the respectively corresponding weight factor assigned to each PDCVS input parameter.

6. The computer-implemented method of claim 5 further comprising:
assigning, for the first user and by the CVS determination machine learning algorithm, a probability that the first user will progress from the first CVS related state to a second CVS related state, based on the plurality of PDCVS input parameter values as weighted by the respectively corresponding weight factor assigned to each PDCVS input parameter.

7. The computer-implemented method of claim 5 wherein the first CVS related state is included in the second set of CVS related state(s) that indicate PDCVS, the further comprising:

responsive to the assignment of the first CVS related state to the first user, sending a communication to the first user including information indicative of a set of remediative action(s) that the first user can take to prevent CVS from developing.

8. The computer-implemented method of claim 5 wherein the first CVS related state is included in the third set of CVS related state(s) that indicate PDCVS, further comprising:

responsive to the assignment of the first CVS related state to the first user, sending a communication to the first user including information indicative of a set of remediative action(s) that the first user can take to counter existing CVS.

9. A computer-implemented method comprising:

receiving a plurality of computer vision syndrome (CVS) input parameters data sets indicating an identity of a plurality of input parameters that may be useful in determining a degree of CVS in users, the plurality of CVS input parameters received from a plurality of external sensors monitoring actions of a user and contextual environment of the user;

receiving a plurality of CVS training data sets (CVS TDSs), with each given CVS TDS including information indicative of: (i) a plurality of CVS values corresponding to the plurality of input parameters, and (ii) an indication of a degree of CVS in an individual that is the subject of the given CVS TDS;

identifying, by a trained CVS determination machine learning algorithm, factors that contribute more, relative to other factors, to CVS of the user based on respective weight factors of the CVS input parameters, the respective weight factors assigned to each CVS input parameter during training of the CVS determination machine learning algorithm, the trained CVS determination machine learning algorithm having been trained by machine logic of an explainable artificial intelligence algorithm (XAI) of a CVS determination machine learning algorithm, to obtain the trained CVS determination machine learning algorithm that is one of structured and programmed to determine a degree of CVS in users based upon the plurality of CVS TDSs; and performing an action selected based on the identified factors of the trained CVS determination machine learning algorithm, wherein the computer implemented method is configured to select the action comprising at least one of recommending remediative actions to the user to prevent CVS and automatically making environmental changes to protect the user from CVS.

10. The computer-implemented method of claim 9 wherein the XAI is a Contrastive Explainability Model type XAI algorithm that includes a Contrastive Explainability Model.

11. The computer-implemented method of claim 9 wherein the XAI uses methods and techniques in an application of artificial intelligence technology (AI) such that results of solutions can be understood by human experts.

12. The computer-implemented method of claim 9 further comprising:

mathematically specifying, in the XAI and by a system designer, a goal system under which weighting factors are determined based upon how much each weighting factor is correlated with a degree of CVS that a user is experiencing.

13. The computer-implemented method of claim 9 wherein the training includes mapping, in the trained CVS determination machine learning algorithm, various degrees of CVS respectively to sets of remediative action(s), if any, to be recommended to users.

14. The computer-implemented method of claim 13 further comprising:

determining, in a first user and by the trained CVS determination machine learning algorithm, a first degree of CVS in the first user; and sending a communication, by the trained CVS determination machine learning algorithm, over a communication network and to the first user, including information indicative of a set of remediative action(s) that have been mapped to the first degree of CVS.

15. The computer-implemented method of claim 9 wherein the plurality of CVS input parameters includes at least one of the following: time spent looking at a display screen, ambient light, display brightness, proximity, time of day and font size.

16. The computer-implemented method of claim 9 wherein the plurality of CVS input parameters includes all of the following: time spent looking at a display screen, ambient light, display brightness, proximity, time of day and font size.

17. A computer-implemented method comprising:

receiving a plurality of computer vision syndrome (CVS) input parameters data sets indicating an identity of a plurality of input parameters that may be useful in determining a degree of computer vision syndrome (CVS) in users, the plurality of CVS input parameters received from a plurality of external sensors monitoring actions of a user and contextual environment of the user;

receiving a plurality of CVS training data sets (TDSs), with each given CVS TDS including information indicative of: (i) a plurality of CVS values corresponding to the plurality of input parameters, and (ii) an indication of a degree of CVS in an individual that is the subject of the given CVS TDS;

training, by machine logic of an explainable artificial intelligence algorithm (XAI), a CVS determination machine learning algorithm to obtain a trained CVS determination machine learning algorithm that is structured and/or programmed to determine a degree of CVS in users based upon the plurality of CVS TDSs, wherein the training includes mapping, in the trained CVS determination machine learning algorithm, various degrees of CVS respectively to sets of remediative action(s), if any, to be recommended to users; and sending a communication, by the trained CVS determination machine learning algorithm, over a communication network to the user, the communication including information indicative of a set of remediative action(s) that have been mapped to a degree of CVS in the user.

18. The computer-implemented method of claim 17 wherein the XAI is a Contrastive Explainability Model type XAI algorithm including a Contrastive Explainability Model (CEM), further comprising:

ranking CVS input parameters with respect to a relative amount of influence a given CVS-related input parameter has upon degradation in state towards CVS;

classifying each CVS-related input parameter resulting in a classification of each CVS-related input parameter;

identifying by the CEM a minimal set of CVS-related input parameters that are sufficient in themselves to yield a same classification; and identifying by the CEM a minimal amount of CVS-related input parameters that should not be considered by the machine logic in rendering determinations of incipient CVS to prevent the classification from changing.

19. The computer-implemented method of claim 17 wherein the XAI uses methods and techniques in an application of artificial intelligence technology (AI) such that results of solutions can be understood by human experts.

20. The computer-implemented method of claim 17 further comprising:

mathematically specifying, in the XAI and by a system designer, a goal system under which weighting factors are determined based upon how much each weighting factor is correlated with a degree of CVS that a user is experiencing.

* * * * *